(12) United States Patent
Chen et al.

(10) Patent No.: US 9,092,055 B2
(45) Date of Patent: Jul. 28, 2015

(54) PLATFORM AND METHOD FOR BCI CONTROL

(75) Inventors: Shih-Chung Chen, Tainan (TW);
Shih-Chang Hsieh, Tainan (TW);
Wei-Jhe Hung, Tainan (TW)

(73) Assignee: SOUTHERN TAIWAN UNIVERSITY, Tainan (TW)

( * ) Notice: Subject to any disclaimer, the term of this patent is extended or adjusted under 35 U.S.C. 154(b) by 552 days.

(21) Appl. No.: 13/415,169

(22) Filed: Mar. 8, 2012

(65) Prior Publication Data
US 2012/0245713 A1    Sep. 27, 2012

(30) Foreign Application Priority Data
Mar. 25, 2011    (TW) .............................. 100110464 A

(51) Int. Cl.
| | |
|---|---|
| G05B 15/00 | (2006.01) |
| G06F 19/00 | (2011.01) |
| A61B 5/04 | (2006.01) |
| A61B 5/00 | (2006.01) |
| A61F 2/70 | (2006.01) |
| G09G 1/08 | (2006.01) |
| G06F 3/033 | (2013.01) |
| G06F 3/01 | (2006.01) |

(52) U.S. Cl.
CPC ...... *G06F 3/015* (2013.01); *G06F 3/01* (2013.01); *A61B 5/00* (2013.01); *G05B 15/00* (2013.01)

(58) Field of Classification Search
CPC .......... G05B 15/00; G06F 19/00; A61B 5/04; A61B 5/0476; A63F 9/24
USPC .................. 700/83, 108, 245; 600/300, 362, 600/544–545; 623/25; 463/36; 345/158, 345/160, 163, 19, 157; 340/825, 19, 157; 901/50
See application file for complete search history.

(56) References Cited

U.S. PATENT DOCUMENTS

| | | | | |
|---|---|---|---|---|
| 5,638,826 | A  * | 6/1997 | Wolpaw et al. | 600/544 |
| 7,120,486 | B2 * | 10/2006 | Leuthardt et al. | 600/545 |
| 2005/0107716 | A1 * | 5/2005 | Eaton et al. | 600/544 |
| 2005/0267597 | A1 * | 12/2005 | Flaherty et al. | 623/24 |
| 2006/0129277 | A1 * | 6/2006 | Wu et al. | 700/245 |

FOREIGN PATENT DOCUMENTS

WO    WO 2012/044261 A1 *    4/2012    ................ G06F 3/01

* cited by examiner

*Primary Examiner* — Mohammad Ali
*Assistant Examiner* — Md Azad
(74) *Attorney, Agent, or Firm* — Muncy, Geissler, Olds & Lowe, P.C.

(57) ABSTRACT

A method for BCI control is utilized to control a plurality of brain control devices. The brain control devices are capable of executing an operation themselves. A brain-wave control platform is provided for supplying a first signal and a second signal, wherein the first and second signals are utilized to visually evoke a user's first and second brain waves, respectively. The brain-wave control platform selects one of the brain control devices as a to-be-controlled device by the first brain wave, and the to-be-controlled device is controlled to finish an operation by the second brain wave.

5 Claims, 6 Drawing Sheets

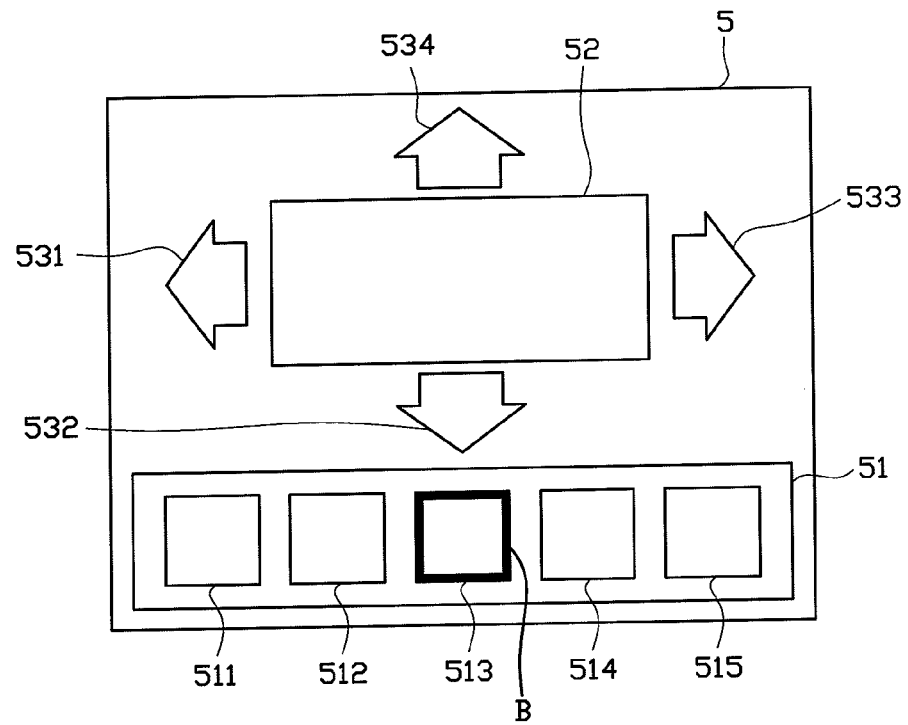
F I G . 3a
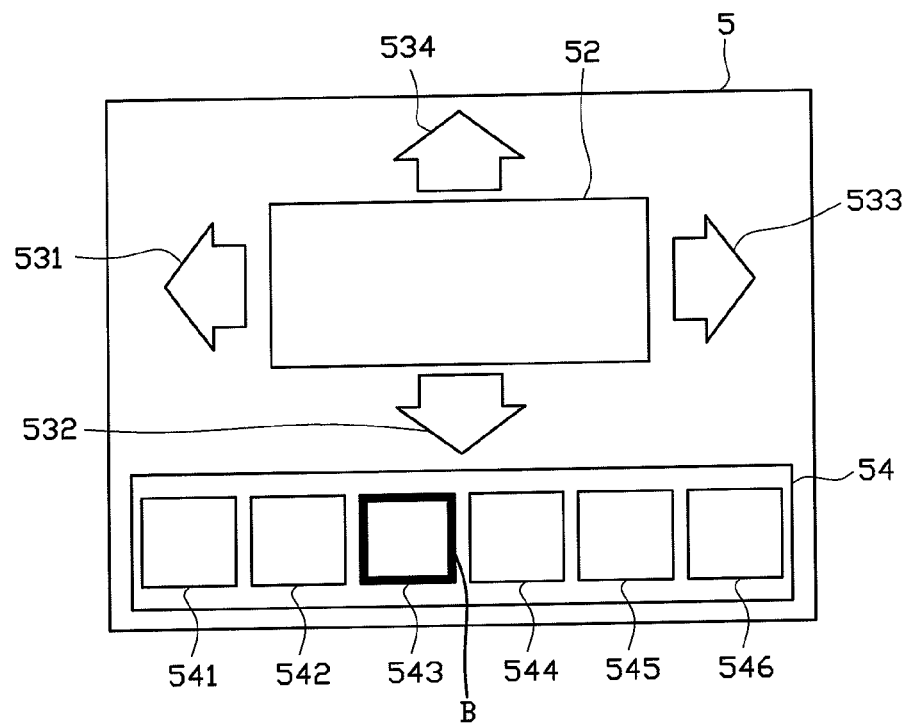
F I G . 3b

PLATFORM AND METHOD FOR BCI CONTROL

BACKGROUND OF THE INVENTION

1. Field of the Invention

The present invention relates to a method for BCI (Brain Computer Interface) control, and in concrete relates to a method for BCI control by utilizing detections of multiple visual evoked potentials to control at least one brain control device.

2. Description of the Related Art

Electronic devices with keyboard input interfaces have been gradually replaced by touch-control input interfaces, and also methods for controlling indexing movements on the display screens are continuously improved. For example, the movement conditions of the joystick of some game commodities can be detected by accelerometers and/or gyroscopes when a user control the joystick, thus to control the actions or motions of the game roles. Some game commodities even use real time image recognition skills instead of the joysticks to identify the commands input from the user and control the movement in the game.

These game commodities mentioned above, the control methods can produce the corresponding control signals until the user executes particular movement by his/her hands or body, but the conveniences of these modern control methods are actually unsuitable for the handicapped. If these devices can be controlled according to the user's brain waves, i.e., move as you think, the handicapped can conveniently manipulate these devices, and the general users can immediately control the movements and operation conditions of the devices according their thoughts.

The present brain wave control (EEG control) techniques are mainly focused on one by one control, i.e., a single control device for controlling a single to-be-controlled device. For controlling the to-be-controlled device one by one, the control device shall be stored with the brain waves representing various instructions for controlling the to-be-controlled device. If planning to control multiple to-be-controlled devices by a single control device, the control device shall be stored with immeasurable and multiple increased brain waves therein. However, the identification accuracy is decreased when the single control device tries to representatively allocate the corresponding instruction to one of the to-be-controlled devices according to the detected brain waves, and it is unfavorable to adding the amount of the control device in this control model. For example, the user intends to turn on the television through the brain wave, but the control device turns on the music players or even turns off the lamps or executes other undesired commands wrongly when receiving the brain wave therefrom.

BRIEF SUMMARY OF THE INVENTION

In view of this, the present inventor devotes himself to the trials and studies to develop a method for BCI control, capable of distinguishing different devices and different control instructions through multiple visual stimulations, selecting the to-be-controlled instruction when the to-be-controlled device is selected by the user, and enhancing the accuracy of the brain wave control (EEG control).

To achieve the purpose above, the present invention provides a method for BCI control, comprising the steps of: providing at least one first stimulation unit utilized to select a brain control device to respectively provide a first stimulation to a user so that the user is enabled to generate a first brain wave to determine a to-be-controlled device; and providing at least one second stimulation unit utilized to select a control instruction to respectively provide a second stimulation to the user so that the user is enabled to generate a second brain wave to determine an operation of the to-be-controlled device.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIGS. 3a, 3b and 3c show display screens of a display unit of an embodiment of the present invention;

DETAILED DESCRIPTION OF THE INVENTION

To further explain the technical content of the present invention, the present invention is described in detail by specific embodiment as follows. A preferred embodiment of the present invention is a method for BCI control.

Figure 1:
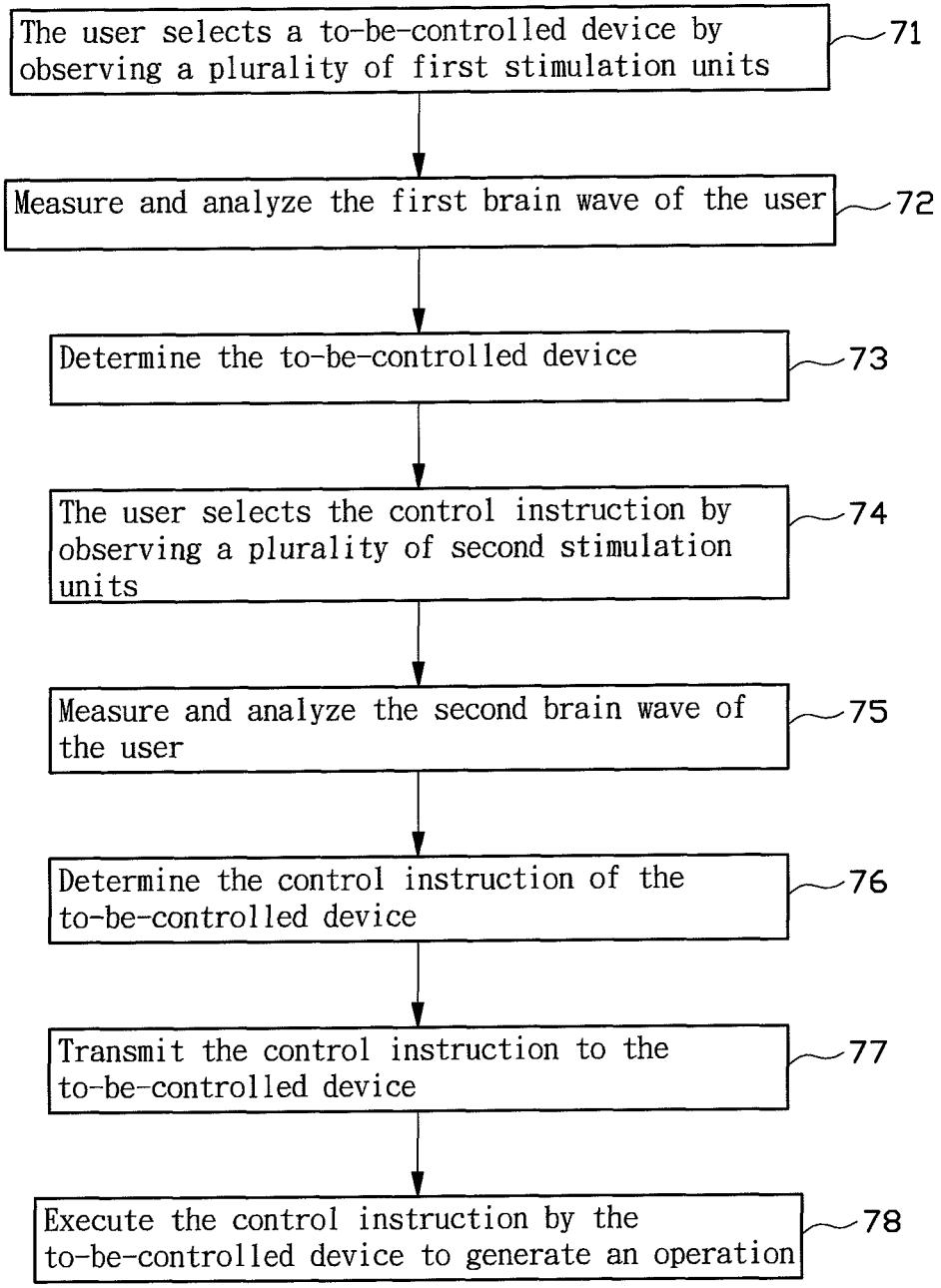
FIG. 1 is a flow chart of a method for BCI control of an embodiment of the present invention.

Referring to FIG. 1, a flow chart of a method for BCI control of an embodiment of the present invention is illustrated. The method comprises the following steps. In step 71, the user selects a to-be-controlled device by his/her own first brain wave (EEG) signal evoked by observing a plurality of first stimulation units. In step 72, the computer measures and analyzes a first brain wave of the user. In step 73, determine the to-be-controlled device. In step 74, the user selects a control instruction by observing a plurality of second stimulation units. In step 75, measure and analyze the second brain wave of the user. In step 76, determine the control instruction of the to-be-controlled device. In step 77, the computer transmits the control instruction to the to-be-controlled device. In step 78, the selected to-be-controlled device executes the selected control instruction to generate an operation.

Referring to FIGS. 1, 2, 3a and 3b simultaneously, in the steps 71, 72 and 73 of FIG. 1 of this embodiment, a device in area 51 of a display screen 5 (in FIG. 3a) located on a display unit 41 (in FIG. 2) is showed with a plurality of brain control device icons 511, 512, 513, 514 and 515 (in FIG. 3a) representing a plurality of brain control devices 451, 452, 453, 454 and 455 (in FIG. 2), so that the user can look attentively at any one of a plurality of stimulation units 531, 532, 533 and 534 which are served as first stimulation units, wherein the stimulation units 531 and 533 are utilized to select the to-be-controlled device (in step 71), and the stimulation units 532 and 534 are utilized to switch the display screen 5 to the next or previous frame. Further, when looking attentively at the stimulation unit 531, the user can leftwards move a bold selection frame 'B' of the brain control device icons 511, 512, 513, 514 and 515; when looking attentively at the stimulation unit 533, the user can rightwards move the bold selection frame 'B' of the brain control device icons 511, 512, 513, 514 and 515. When the user moves the bold selection frame 'B' to the to-be-controlled brain control device by looking attentively at the stimulation unit 531 or 533, the display screen 5 is switched to the next frame if further looking attentively at the stimulation unit 532 to determine the brain control device, or the display screen 5 is switched to the previous frame if further looking attentively at the stimulation unit 534 to determine the brain control device. The computer analyzes different brain waves generated from the user (in step 72) to determine the to-be-controlled device (in step 73) based on the different visual stimulations provided by the stimulation units. For example, if the user plans to control the third brain control device 453 (in FIG. 2), the user can correspondingly observe or look attentively at the shift-right-selection 533 stimulation unit (in FIG. 3a) or the shift-left-selection 531 stimulation unit, so that a first brain wave of the user is generated when the user's eyes are stimulated by the stimulation unit and a selected region 52 of the display screen 5 (in FIG. 3a) is showed with the brain control device icon 513 presented with the bold selection frame 'B'. Then, the user can look attentively at the stimulation unit 532 which is corresponding to the selected operation to determine the selected to-be-controlled device to enter the next level of the display screen.

Figure 2:
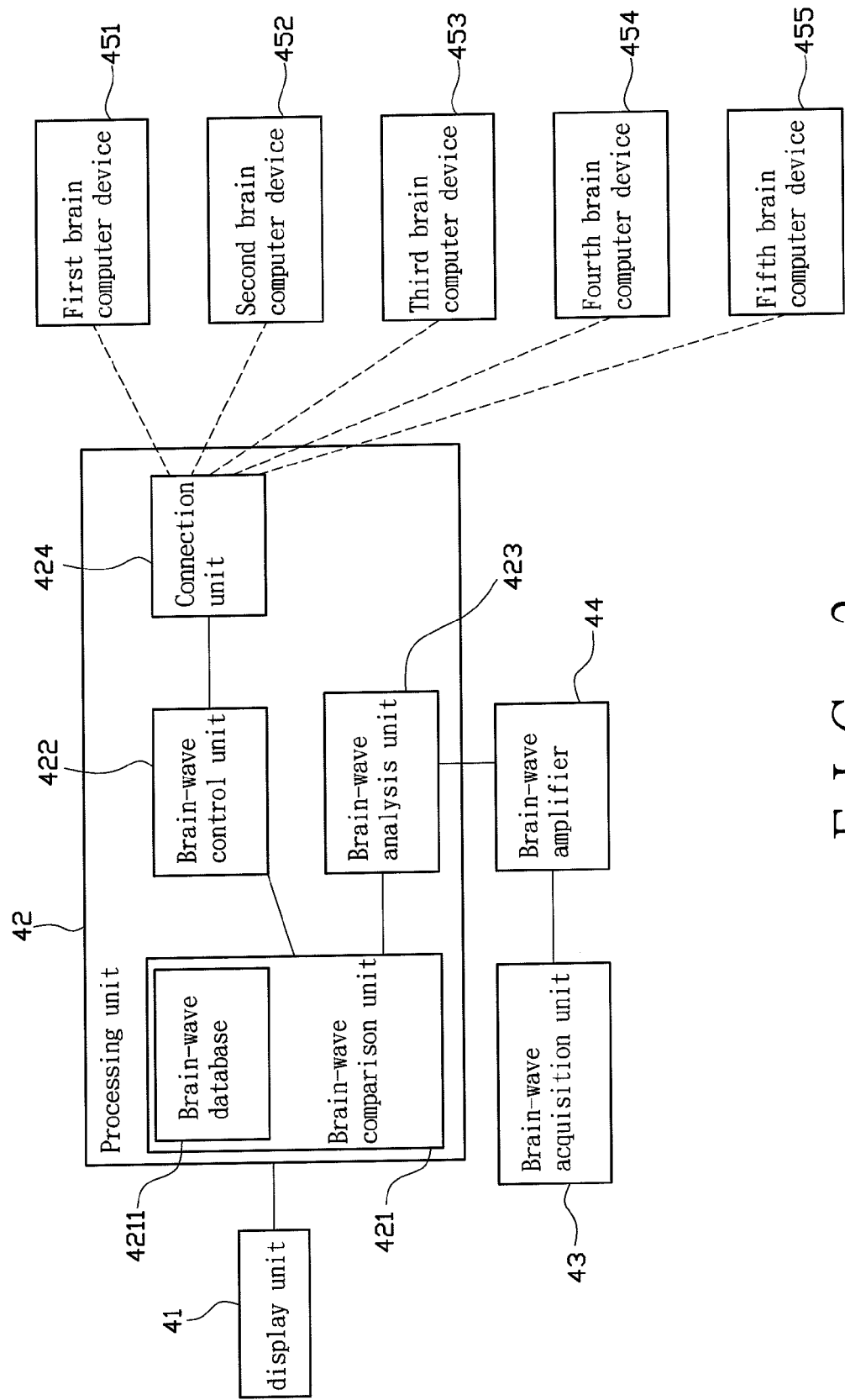
FIG. 2 is schematic view showing a system of a method for BCI control of the present invention.
Figure 3C:
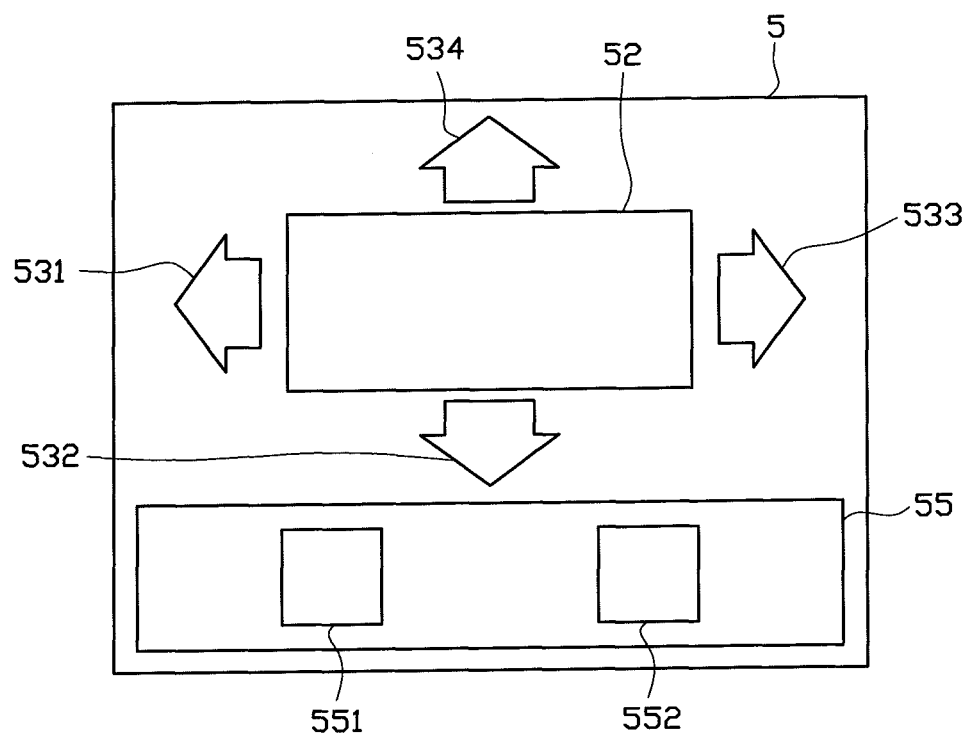

In steps 74, 75 and 76, due to the to-be-controlled device which is already determined in step 73, a control region 54 of the display screen 5 (in FIG. 3b) on the display unit 41 (in FIG. 2) is showed with a plurality of controls 541, 542, 543, 544, 545 and 546 representing a plurality of control operations, and the user can look attentively at any one of the stimulation units 531, 532, 533 and 534 which are served as a plurality of second stimulation units, wherein the stimulation units 531 and 533 are utilized to select the control operations to be performed (in step 74), and the stimulation units 532 and 534 are utilized to switch the display screen 5 to the next or previous frame. Further, when looking attentively at the stimulation unit 531, the user can leftwards move a bold selection frame 'B' of the brain control device icons 541, 542, 543, 544, 545 and 546; when looking attentively at the stimulation unit 533, the user can rightwards move the bold selection frame 'B' of the brain control device icons 541, 542, 543, 544, 545 and 546. When the user moves the selection frame 'B' to the to-be-controlled brain control device by looking attentively at the stimulation unit 531 or 533, the display screen 5 is switched to the next frame if further looking attentively at the stimulation unit 532 to determine the brain control device, or the display screen 5 is switched to the previous frame if further looking attentively at the stimulation unit 534 to determine the brain control device. The stimulation units 531, 532, 533 and 534 served as the second stimulation units can provide different visual stimulations to enable the user to generate the second brain wave for analysis (in step 75), and then the control operations can be selected (in step 76). Referring to FIG. 2, the first and second brain waves are to be accessed by a brain-wave acquisition unit 43, amplified by a brain-wave amplifier 44, and transmitted to a processing unit 42. A brain-wave analysis unit 423 is utilized to analyze the first brain wave or the second brain wave received by the processing unit 42, thus to obtain a first visual evoked potential or a second visual evoked potential. Then, the analyzed result transmitted from the brain-wave analysis unit 423 is received by a brain-wave comparison unit 421 and compared to a brain-wave signal which is served as a reference value stored in a brain-wave database 4211 of the brain-wave comparison unit 421, thereby confirming the control instruction selected by the user.

In step 77 of FIG. 1, due to the to-be-controlled device and the control instruction thereof which are already determined by the processing unit 42 (in FIG. 2), the control instruction is transmitted to the to-be-controlled device via a connection unit 424, and the to-be-controlled device in step 78 executes the operation corresponding to the control instruction when receiving the control instruction.

The processing unit 42 is designed to determine the information or instruction showed on the display unit 41, such as the visual stimulations, the to-be-controlled instruction for transmitting to the to-be-controlled device and various brain-wave processing for analyzing and explaining the user's brain waves.

In the processing unit 42, the brain-wave database 4211 of the brain-wave comparison unit 421 can be utilized to store the brain-wave signals as comparison pattern for the user's brain waves. In a particular embodiment, because the brain wave is evoked by the visual stimulations in a brain-wave control system, the brain-wave database 4211 of the brain-wave comparison unit 421 can be only utilized to store all applied visual stimulations of the brain control system.

In the processing unit 42, the brain-wave comparison unit 421 is utilized to compare the analyzed first and second brain waves to the brain-wave pattern stored in the brain-wave database 4211, thereby confirming the representative stimulation signals for the first and second brain waves. The brain-wave comparison unit 421 is coupled to a brain-wave control unit 422 and the brain-wave analysis unit 423. When receiving the analyzed first and/or second brain waves and the brain-wave patterns of the brain-wave database 4211, the brain-wave comparison unit 421 can render the brain-wave analysis comparison result therebetween to the brain-wave control unit 422.

The brain-wave control unit 422 is utilized to generate the control instruction to control the to-be-controlled device. The brain-wave control unit 422 still has to couple to the brain-wave comparison unit 421 and the connection unit 424 if the control instruction is stored in the brain-wave control unit 422, thereby understanding the brain-wave comparison result to determine the to-be-controlled device and the control instruction and transmitting the control instruction via the connection unit 424.

As mentioned above, the brain-wave analysis unit 423 is utilized to analyze the received first and second brain waves. Therefore, the brain-wave analysis unit 423 shall be coupled to the wave-brain amplifier 44, so that the brain-wave analysis unit 423 can access the received brain-wave signals from the wave-brain amplifier 44. Besides, the brain-wave analysis unit 423 is also coupled to the brain-wave comparison unit 421, so that the analyzed result transmitted from the brain-wave analysis unit 423 can be transmitted to the brain-wave comparison unit 421. The brain-wave analysis unit 423 can be provided with a wired or wireless connection port, so that the brain-wave analysis unit 423 can be coupled to the brain wave amplifier 44 via a wired or wireless connection.

The connection unit 424 is utilized to connect the brain control devices 451-455. In one embodiment, the connection unit 424 can be connected via a wired communication interface such as Universal Serial Bus (USB) interface and Transmission Control Protocol/Internet Protocol (TCP/IP), or a wireless communication system.

The brain-wave acquisition unit 43 is disposed on the user's head for detecting the brain waves transmitted therefrom. In this embodiment, the brain-wave acquisition unit 43 comprises a plurality of detection electrodes.

The wave-brain amplifier 44 is utilized to amplify the signal of the brain wave accessed from the brain-wave acquisition unit 43, and the amplified signal of the brain wave is provided to the processing unit 42 for analysis and control, wherein the brain wave amplifier 44 can be directly in signal communication with the brain-wave analysis unit 423 of the processing unit 42.

The brain control devices 451-455 are utilized to receive the control instructions transmitted from the connection unit 424, thereby performing the operations controlled by the control instructions. When the control instructions provided by the connection unit 424 is based on one of the brain control devices 451-455, the rest of the brain control devices shall be remained the original status thereof and not be controlled by a brain-wave control platform.

Figure 4:
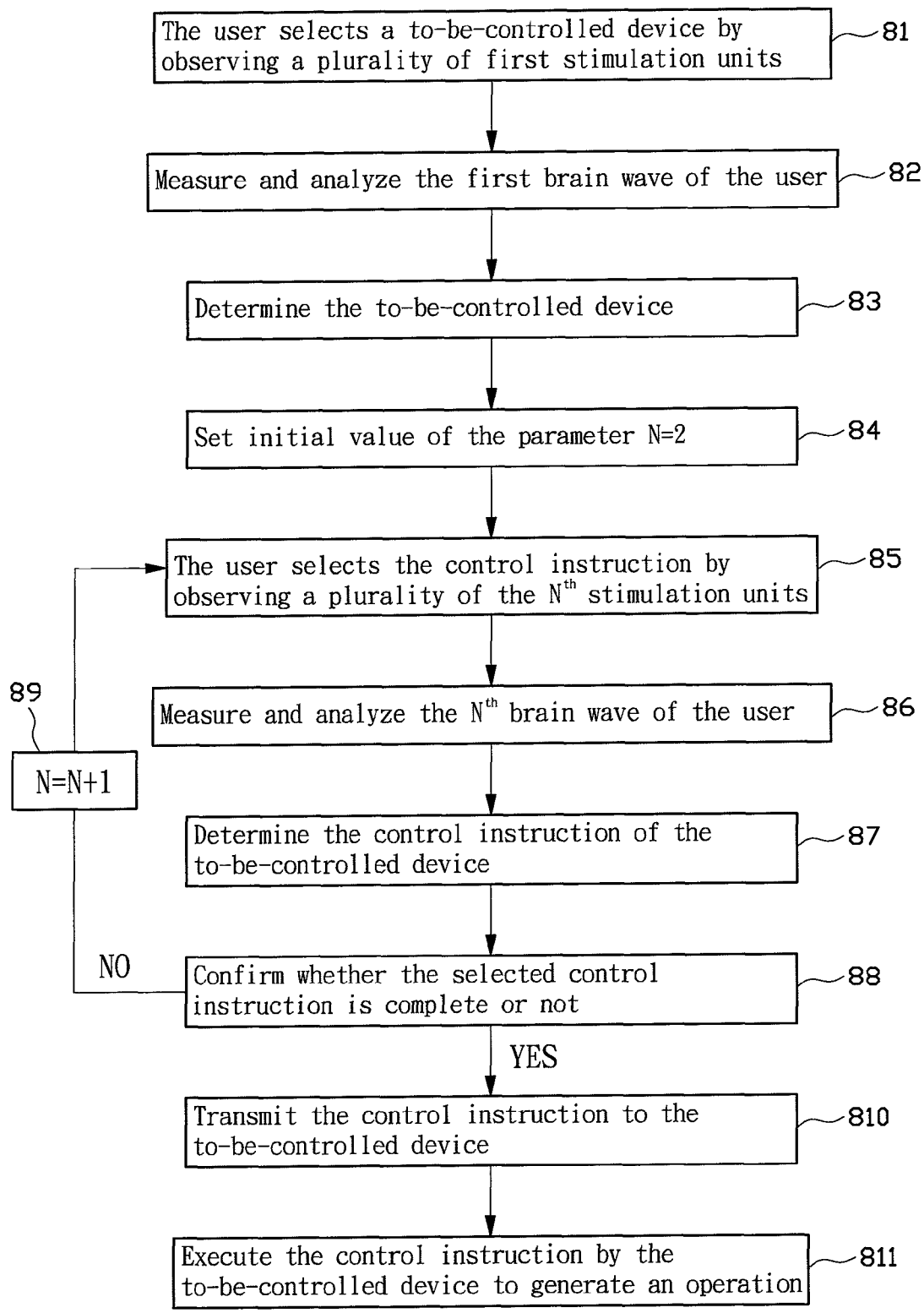
FIG. 4 is a flow chart of a method for BCI control of an embodiment of the present invention.

Referring to FIG. 4, a flow chart of a method for BCI control of another embodiment is illustrated, wherein the method comprises steps 81, 82, 83, 84, 85, 86, 87, 88, 89, 810 and 811. Referring to FIGS. 1, 2, 3c and 4 simultaneously, the steps in FIG. 4 differs from that in FIG. 1 is that steps 85-89 constitutes a circle loop, and step 84 is an initial setting step related to the circle loop of steps 85-89. Steps 81-83 and steps 810-811 in FIG. 4 respectively correspond to steps 71-73 and 77-78 in FIG. 1. In this embodiment, in step 84 the 'N' is set as two after the steps 81-83 are finished, so that the circle loop of steps 85-89 can be smoothly performed. In step 85, the user observes the $N^{th}$ brain wave. In step 86, the brain control platform measures and analyzes the $N^{th}$ brain wave generated from the user. In step 87, the brain control platform confirms the control instruction selected by the user by analyzing the $N^{th}$ brain wave. In step 88, the brain control platform confirms whether the selected control instruction is complete or not. If the selected control instruction is not complete, return repeatedly to step 85 via step 89 and let 'N' being equal to 'N+1' so as to perform the brain-wave stimulation and the brain-wave detection in the next stage. If the selected control instruction is complete, perform step 810 which is corresponding to step 77 in FIG. 1. In the embodiment above, the incomplete control instruction mainly refers that the second brain wave still cannot specifically identify the condition of the control instruction of the to-be-controlled device, for example, the second brain wave only selects the volume adjustment but not decide to turn up or down the volume. At this moment, an instruction region 55 (in FIG. 3c) can further provide options to select a first control instruction 551 or a second control instruction 552, i.e., from step 89 back to step 85, wherein equally the stimulation units 531-534 are utilized to select the to-be-controlled brain control device, and the visual stimulations enable the user to generate the third brain wave to fulfill the selection of the control instruction. Similarly, when the brain control platform requires the fourth brain wave or even fifth brain wave in use, it is applicable, the same as the embodiment above, by performing the circle loop operation of the brain-wave stimulation and the brain-wave detection. In the embodiment above, as the same as the first brain wave, the third brain wave or even fourth brain wave is accessed by the brain-wave acquisition unit 43, amplified by the wave-brain amplifier 44 and then transmitted to the processing unit 42.

Figure 5:
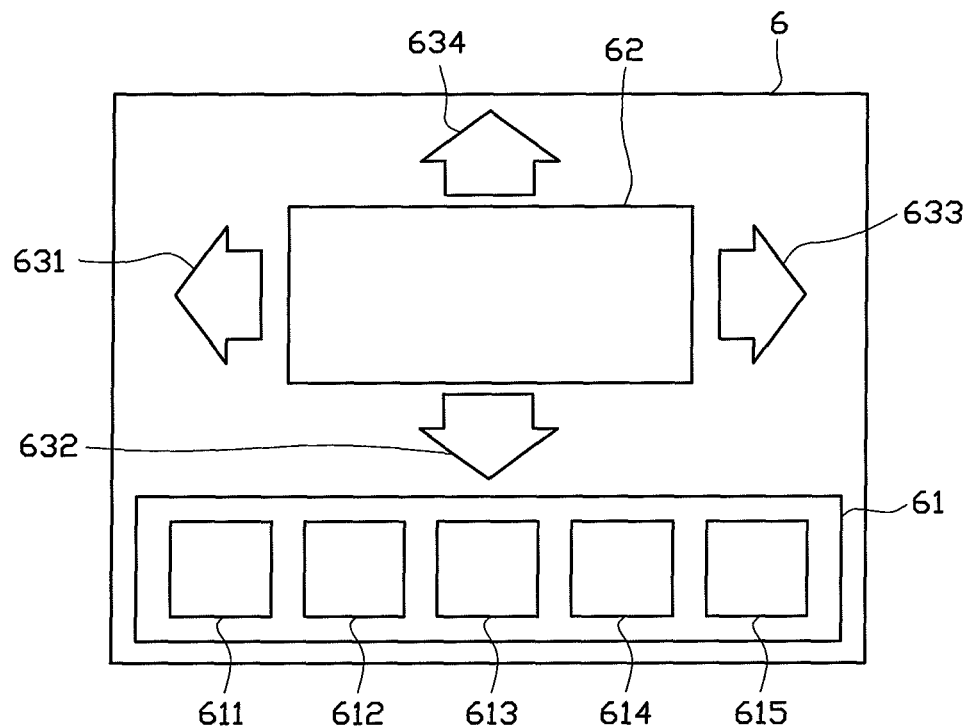
FIG. 5 shows a display screen of a display unit of an embodiment of the present invention.

Referring to FIGS. 1, 4 and 5 simultaneously, another embodiment is provided. In step 71 (in FIG. 1), it can be acquired that, on the display unit 41, a plurality of first stimulation units 611, 612, 613, 614 and 615 representing the brain control devices 451, 452, 453, 454 and 455 of FIG. 2 are shown on a first stimulation region 61 of a display screen 6 (in FIG. 5), and each of the first stimulation units 611, 612, 613, 614 and 615 can provide different visual stimulations to cause the user to generate different brain waves. If planning to control the third brain control device 453 (in FIG. 2), the user can observe or look attentively at the first stimulation unit 613 which is corresponding to the third brain control device 453 to generate a first brain wave while the user's eyes are stimulated by the first stimulation unit 613, thereby determining the selection of the to-be-controlled device.

In step 72, due to the first brain wave of the user being formed when the user is stimulated by one of the first stimulation units 611-615, the first brain wave is then accessed by the brain-wave acquisition unit 43 (in FIG. 2), amplified by the wave-brain amplifier 44, and transmitted to the processing unit 42. When the processing unit 42 receives the amplified first brain wave, the brain-wave analysis unit 423 analyzes the first brain wave to obtain a first visual evoked potential.

In step 73, the analyzed result transmitted from the brain-wave analysis unit 423 is received by the brain-wave comparison unit 421 and compared to the brain-wave signal which is served as a reference value stored in a brain-wave database 4211 of the brain-wave comparison unit 421, thereby confirming the control instruction selected by the user from at least one of the brain control devices 451, 452, 453, 454 and 455 and further setting the selected brain control device as a to-be-controlled device.

In step 74, due to the to-be-controlled device which is already determined in step 73, the second stimulation units can be respectively showed with the control instructions representing corresponding operations of the selected to-be-controlled device, and the second stimulation units are respectively provided with different visual stimulations, thereby enabling the user to generate different brain waves. If the user decides to perform a control instruction which is corresponding to the second visual stimulation 634, the user can observe or look attentively at the second stimulation unit 634 to generate a second brain wave while the user's eyes are stimulated by the second stimulation unit 634, thereby determining the control instruction selection of the selected to-be-controlled device. Also, the user can observe or look attentively at one of the second stimulation units 611-615 to generate a second brain wave while the user's eyes are stimulated by the second stimulation units 611-615, thereby determining the control instruction selection of the selected to-be-controlled device.

In step 75, due to the second brain wave of the user being generated because the user is stimulated by one of the second stimulation units 631-634 or 611-615 in step 74, the second brain wave is then accessed by the brain-wave acquisition unit 43, amplified by the wave-brain amplifier 44, and transmitted to the processing unit 42. When the processing unit 42 receives the amplified second brain wave, the brain-wave analysis unit 423 analyzes the second brain wave to obtain a second visual evoked potential.

In step 76, the analyzed result transmitted from the brain-wave analysis unit 423 is received by the brain-wave comparison unit 421 and compared to the brain-wave signal which is served as a reference value stored in a brain-wave database 4211 of the brain-wave comparison unit 421, thereby confirming the control instruction selected by the user and further determining the next operation of the selected to-be-controlled device.

In step 77, due to the to-be-controlled device and the control instruction thereof which are already determined by the processing unit 42, the control instruction is transmitted to the to-be-controlled device via the connection unit 424, and the to-be-controlled device in step 78 executes the operation corresponding to the control instruction when receiving the control instruction.

In the embodiment above, the display unit 41, the brain-wave acquisition unit 43 and the wave-brain amplifier 44 can be coupled to the processing unit 42 via wired or wireless connection for various signal transmissions. In another embodiment, the wave-brain amplifier 44 can be directly combined with the brain-wave acquisition unit 43 as a single component, capable of simultaneously executing the signal accessing and amplifying functions. In yet another embodiment, the wave-brain amplifier 44 can be omitted if the signal accessed by the brain-wave acquisition unit 43 is sufficient to execute the analysis process, and the brain-wave acquisition unit 43 can be directly in signal communication with the processing unit 42.

In the aspect of signal processing of BCI (Brain Computer Interface), the accessed signal shall be processed by a baseline calibration if the accessed signal has baseline drifts. A baseline of the signal shall be first calculated by the brain-computer, and then the accessed signal minus the calculated baseline leaves a calibrated brain wave signal, thereby improving the baseline drifts. In general, the detected brain waves are contained with interferences having particular noises such as eye-movement signals generated by blinking, and a method such as Independent Component Analysis (ICA) can be utilized to eliminate the particular noises mixed in the brain waves during the determining process. The ICA method is the one utilized algorithm to restore the linear mixed signals into several fundamental signal sources. Assumed that x(t) is an observation signal matrix composed of mixed signals with different channels and s(t) is a signal source matrix composed of mutually independent signal sources, each observation signals can be expressed by $x_i(t) = a_{i1}s_1(t) + a_{i2}s_2(t) + \ldots + a_{im}s_m(t)$, wherein i=1, ..., n. This formula $x_i(t)$ can be expressed in matrix by:

$$\begin{bmatrix} x_1(t) \\ \vdots \\ x_n(t) \end{bmatrix} = \begin{bmatrix} a_{11} & \cdots & a_{1m} \\ \vdots & \vdots & \vdots \\ a_{n1} & \cdots & a_{nm} \end{bmatrix} \begin{bmatrix} s_1(t) \\ \vdots \\ s_m(t) \end{bmatrix} \quad (1)$$

The matrix (1) can be briefly expressed by x(t)=As(t), wherein 'A' represents a n×m mixed matrix constituted by coefficient '$a_{ij}$'. It is understood that the signal source matrix can be obtained by calculating the observed signal vector x(t) and the mixed matrix 'A'. Then, after setting the particular noises such as eye-movement signals which are needed to be deducted from the signal source matrix as zero, an observation signal vector without the particular noises (e.g., eye-movement signals) can be obtained by recalculating the signal source matrix and the mixed matrix 'A'. Unnecessary interferences in the signal can be filtered by a first filter (e.g., various bandpass filters), and the signals are divided into fixed length at different time periods and accumulatively averaged therewith according to the time spots required to be analyzed. The signals processed by the accumulated average method can be qualified with high signal-noise ratio, and it relatively takes a longer period of time when the signals are accumulatively averaged. Thus, it is important to get a balance between the processing time and the signal-noise ratio when processing the signals.

Some noises are occurred when the signals are accumulatively averaged, and these noises can be filtered by a second filter, preferably using a Savitzky-Golay filter. With a least-squares polynomial regression method provided by the Savitzky-Golay filter, the signal data are treated in a smoothing process, and the mathematical formula thereof is expressed by:

$$\overline{g}(t) = \sum_{i=n_L}^{n_R} c_i \times f(t+i) \quad (2)$$

In formula (2), '$\overline{g}(t)$' represents the signal smoothing value at time 't', 'i', represents the time index value at time 't', '$n_L$' represents the time index before time 't', '$n_R$' represents the time index value after time 't', '$c_i$' represents the weighting coefficient matrix, and 'f(t)' represents the actual signal value at 't'. Further, the Savitzky-Golay filter is served as a low-pass filter capable of reducing noises. On the general condition of the smoothing process, the Savitzky-Golay filter can reduce the possible distortions in the filtering process and preserve the signal features such as maximum and minimum values and width of the signal data etc. Moreover, for reducing the recognition time and increasing the legibility on the features of brain wave signal, a mean envelope method can be further applied to form a local maximum value and a local minimum value of signals into an upper envelope line and a lower envelope line in the type of cubic arc; moreover, a mean envelope line can be obtained by averaging the upper envelope line and the lower envelope line, thus to enhance the recognizable difference of the visual evoked potential. At last, the average value of the upper and lower envelope lines is analyzed to obtain the intensity relationship between the signal and the prestored information by the correlation coefficient analytical method, compared to the preset threshold value. If the intensity relationship between the signal and the prestored information after the correlation coefficient analytical calculation is greater or equal to the preset threshold value, the control instruction is allowed to transmit to the brain control device.

In the embodiment above, at least one brain control device can be a brain-controlled page turner, a brain-controlled hospital bed, a brain-controlled music player, a brain-controlled feeding machine, a brain-controlled mouse, a brain-controlled wheel chair, a brain-controlled amusement device and/or a general home appliance comprising a television, an air conditioner and a fan. The brain control devices can have various control instructions according to the different requirements. For example, the control instructions of the brain-controlled page turner can have various operation modes such as right turn mode, and left turn mode. The brain-controlled music player can have various control instructions such as turn-on mode, turn-off mode, play mode, pause mode, volume turn up mode, volume turn down mode, select mode and repeat mode, etc.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

What is claimed is:

1. A method for brain-computer interface control, comprising:
   displaying, on a display screen, a plurality of first stimulation units utilized to select a brain control device, each of said plurality of first stimulation units providing a respective first stimulation and thus enabling a user to generate a respective first brain wave while a visual attention of the user is directed to the display screen;
   analyzing the respective first brain wave elicited by said each of said plurality of first stimulation units and determining a to-be-controlled device based upon a result of said analyzing the respective first brain wave;

displaying, on the display screen, a plurality of second stimulation units utilized to select a control instruction to the determined to-be-controlled device, each of said plurality of second stimulation units providing a respective second stimulation and thus enabling the user to generate a respective second brain wave while the visual attention of the user is directed to the display screen; and analyzing the respective second brain wave elicited by said each of said plurality of second stimulation units and determining an operation of the determined to-be-controlled device based upon a result of said analyzing the respective second brain wave, wherein said analyzing the respective first brain wave and said analyzing the respective second brain wave utilize a mean envelope method in which a mean envelope line is obtained by averaging an upper envelope line and a lower envelope line, and wherein the upper envelope line and the lower envelope line are formed, in a cubic arc, by capturing local maximum values and local minimum values respectively, of the first brain wave and/or the second brain wave.

2. The method for brain-computer interface control as claimed in claim 1 further comprising:

analyzing the first brain wave to generate a first visual evoked potential and comparing a plurality of reference values to determine the to-be-controlled device from at least one brain control device; and analyzing the second brain wave to generate a second visual evoked potential and comparing the reference values to determine an operation of the determined to-be-controlled device.

3. The method for brain-computer interface control as claimed in claim 2, characterized in that the user generates the first brain wave in response to the first stimulation corresponding to the to-be-controlled device, and the user generates the second brain wave in response to the second stimulation corresponding to the operation.

4. The method for brain-computer interface control as claimed in claim 2, wherein said analyzing the respective first brain wave and said analyzing the respective second brain wave utilize an ICA (independent component analysis method), a first filter, a built-up average method, and/or a second filter, and the brain control devices comprise a brain-controlled page turner, a brain-controlled hospital bed, a brain-controlled music player, a brain-controlled feeding machine, a brain-controlled mouse, a brain-controlled wheel chair, a brain-wave amusement device and/or a general home appliance comprising a television, an air conditioner and a fan.

5. The method for brain-computer interface control as claimed in claim 4, wherein said analyzing the respective first brain wave and said analyzing the respective second brain wave utilize a baseline drift calibration, in which a baseline of the respective first brain wave is calculated to be subtracted from the respective first brain wave so as to obtain a calibrated first brain wave, and in which a baseline of the respective second brain wave is calculated to be subtracted from the respective second brain wave so as to obtain a calibrated second brain wave.

* * * * *